US010646669B2

(12) United States Patent
Egan et al.

(10) Patent No.: US 10,646,669 B2
(45) Date of Patent: May 12, 2020

(54) AEROSOL MEDICATION DELIVERY SYSTEM AND METHOD

(71) Applicant: ONY Biotech Inc., Amherst, NY (US)

(72) Inventors: Edmund A. Egan, Amherst, NY (US); William H. Ferguson, Tonawanda, NY (US)

(73) Assignee: ONY BIOTECH INC., Amherst, NY (US)

( * ) Notice: Subject to any disclaimer, the term of this patent is extended or adjusted under 35 U.S.C. 154(b) by 296 days.

(21) Appl. No.: 15/540,203

(22) PCT Filed: Dec. 28, 2015

(86) PCT No.: PCT/US2015/067600
§ 371 (c)(1),
(2) Date: Jun. 27, 2017

(87) PCT Pub. No.: WO2016/109390
PCT Pub. Date: Jul. 7, 2016

(65) Prior Publication Data
US 2017/0368276 A1    Dec. 28, 2017

Related U.S. Application Data

(60) Provisional application No. 62/097,522, filed on Dec. 29, 2014.

(51) Int. Cl.
A61M 16/12    (2006.01)
A61M 15/00    (2006.01)
(Continued)

(52) U.S. Cl.
CPC ........ A61M 15/0085 (2013.01); A61M 16/04 (2013.01); A61M 16/0858 (2014.02);
(Continued)

(58) Field of Classification Search
CPC ..... A61B 1/00154; A61B 1/24; A61B 5/0823; A61B 5/087; A61B 5/097; A61B 5/4839;
(Continued)

(56) References Cited

U.S. PATENT DOCUMENTS 4,030,493 A * 6/1977 Walters ............. A61M 16/0488
128/206.21
4,270,531 A * 6/1981 Blachly ............. A61M 16/0488
128/207.14
(Continued)

Primary Examiner — Annette Dixon
(74) Attorney, Agent, or Firm — Hodgson Russ LLP

(57) ABSTRACT

Systems and methods are disclosed for delivering medication to a patient. One such system has an aerosol generator for aerosolizing medication. The generator is located outside the airway of a patient. A chamber is provided for receiving aerosolized medication from the generator. The system has a carrier gas supply tube for delivering carrier gas to the chamber, and an aerosol delivery tube for receiving the aerosolized medication and the carrier gas from the chamber. The aerosol delivery tube delivers the aerosolized medication to the patient. A distal end of the aerosol delivery tube is positioned inside the airway of the patient in order to discharge the aerosolized medication within the patient's airway.

28 Claims, 7 Drawing Sheets

(51) Int. Cl.
*A61M 16/08* (2006.01)
*A61M 16/04* (2006.01)
*A61M 16/14* (2006.01)
*A61M 16/00* (2006.01)

(52) U.S. Cl.
CPC .......... *A61M 16/12* (2013.01); *A61M 16/142* (2014.02); *A61M 2016/0027* (2013.01); *A61M 2202/0208* (2013.01); *A61M 2240/00* (2013.01)

(58) Field of Classification Search
CPC . A61B 5/7282; A61J 15/0003; A61J 15/0061; A61J 17/001; A61J 17/006; A61J 2200/76; A61J 7/0053; A61M 11/002; A61M 11/02; A61M 11/06; A61M 15/00; A61M 15/0015; A61M 15/0021; A61M 15/0036; A61M 15/0086; A61M 15/009; A61M 15/0091; A61M 15/0093; A61M 15/08; A61M 16/0051; A61M 16/0057; A61M 16/024; A61M 16/0488; A61M 16/049; A61M 16/0493; A61M 16/0495; A61M 16/06; A61M 16/0816; A61M 16/0833; A61M 16/085; A61M 16/10; A61M 16/12; A61M 16/14; A61M 16/16; A61M 16/201; A61M 16/202; A61M 16/209; A61M 2016/0024; A61M 2016/0027; A61M 2016/0039; A61M 2202/0007; A61M 2202/0208; A61M 2202/0283; A61M 2205/13; A61M 2205/3561; A61M 2205/3569; A61M 2205/3592; A61M 2205/502; A61M 2205/52; A61M 2205/59; A61M 2205/6063; A61M 2205/8218; A61M 2205/8225; A61M 2206/14; A61M 2230/432; A61M 2240/00

See application file for complete search history.

(56) References Cited

U.S. PATENT DOCUMENTS

| | | | | |
|---|---|---|---|---|
| 5,146,913 | A * | 9/1992 | Khorsandian | A61M 16/0488 128/200.26 |
| 5,181,505 | A * | 1/1993 | Lew | A61M 16/04 128/200.26 |
| 5,626,128 | A * | 5/1997 | Bradley | A61M 16/0488 128/200.26 |
| 5,685,291 | A | 11/1997 | Marsh | |
| 5,810,000 | A * | 9/1998 | Stevens | A61M 16/0488 128/200.24 |
| 5,904,140 | A * | 5/1999 | McGoogan | A61M 15/08 128/200.24 |
| 6,776,157 | B2 * | 8/2004 | Williams | A61B 1/00154 128/200.26 |
| 2003/0196660 | A1 * | 10/2003 | Haveri | A61M 15/0085 128/203.12 |
| 2004/0011358 | A1 | 1/2004 | Smaldone et al. | |
| 2005/0217678 | A1 * | 10/2005 | McCormick | A61M 16/06 128/206.29 |
| 2008/0257337 | A1 * | 10/2008 | Denyer | A61M 11/005 128/200.14 |
| 2009/0056721 | A1 * | 3/2009 | Leboeuf | A61M 16/0488 128/207.14 |
| 2010/0282247 | A1 * | 11/2010 | Kadrichu | A61K 9/0078 128/200.14 |
| 2012/0048264 | A1 | 3/2012 | Finlay et al. | |
| 2013/0000641 | A1 | 1/2013 | Mazela et al. | |
| 2013/0333695 | A1 | 12/2013 | Dellaca et al. | |
| 2016/0199609 | A1 * | 7/2016 | Gulka | A61M 16/0495 128/200.23 |
| 2017/0143590 | A1 * | 5/2017 | Smith | A61J 17/006 |

* cited by examiner

```
┌─────────────────────────────┐
│ GENERATE AN AEROSOL FROM A LIQUID │
│ MEDICATION TO PROVIDE AN AEROSOLIZED │
│ MEDICATION.                 │
└─────────────────────────────┘ — 100
              │
              ▼
┌─────────────────────────────┐
│    PROVIDE A CARRIER GAS.   │
└─────────────────────────────┘ — 103
              │
              ▼
┌─────────────────────────────┐
│     FLOW THE CARRIER GAS.   │
└─────────────────────────────┘ — 106
              │
              ▼
┌─────────────────────────────────────┐
│ CONVEY THE AEROSOLIZED MEDICATION USING │
│ THE CARRIER GAS VIA A DELIVERY TUBE TO A │
│ DISTAL END OF THE DELIVERY TUBE, WHICH HAS │
│ BEEN PLACED IN THE PATIENT'S AIRWAY. │
└─────────────────────────────────────┘ — 109
              │
              ▼
┌─────────────────────────────┐
│ DISCHARGE THE AEROSOLIZED   │
│ MEDICATION AND CARRIER GAS IN THE │
│ PATIENT'S AIRWAY.           │
└─────────────────────────────┘ — 112
```

Fig. 5

AEROSOL MEDICATION DELIVERY SYSTEM AND METHOD

CROSS-REFERENCE TO RELATED APPLICATION

This application claims the benefit of priority to U.S. provisional patent application Ser. No. 62/097,522, filed on Dec. 29, 2014.

FIELD OF THE INVENTION

The present invention relates to devices, systems, and methods of delivering medication to a patient.

BACKGROUND OF THE INVENTION

Existing systems for delivering aerosolized medication to a patient are commonly in two forms. In one form, the medication is aerosolized outside the airway of the patient, and then delivered into a breathing gas delivery system, which mixes the aerosolized medication with the breathing gas prior to its being inhaled by the patient. For example, see U.S. Publ. No. US2012/0048264 (Finlay et al.). In another form, the medication is aerosolized in the patient's airway at the tip of a multi-lumen cannula, which transports gas and liquid medication to the tip in separate channels. For example, see U.S. Publ. No. US2013/0333695 (Dellaca et al.). These systems can be inefficient and potentially unsafe to use, especially with regard to newborns.

SUMMARY OF THE INVENTION

The invention may be embodied as a system for delivering medication to a patient. Such a system may include an aerosol generator (sometimes referred to merely as "generator") for aerosolizing medication. The aerosol generator may be located outside the airway of the patient. The system may include a chamber for receiving the aerosolized medication from the generator, and a carrier gas supply tube may be used for delivering a carrier gas to the chamber. The chamber may be located proximal to the patient.

An aerosol delivery tube may be provided for receiving the aerosolized medication and the carrier gas from the chamber, and delivering the aerosolized medication and carrier gas to the patient. A distal end of the aerosol delivery tube may be positioned inside the airway of the patient, for example in the oropharyngeal cavity of the patient, in order to discharge the aerosolized medication within the patient's airway. Alternatively, the distal end of the aerosol delivery tube may be positioned at or slightly beyond a distal end of an endotracheal tube that is inserted in the patient. Such an arrangement within an endotracheal tube may be accomplished by passing the aerosol delivery tube into the endotracheal tube via a port at a proximal end of the endotracheal tube, or through a port of an endotracheal tube adapter, or through a port of a patient respiratory support circuit. The distal end of the aerosol delivery tube may be positioned at or slightly beyond the distal end of the endotracheal tube.

As used herein, the phrase "proximal end" and the phrase "distal end" are used with reference to the generator. As such, the "proximal end" of a tube is closer to the generator than is the "distal end" of that tube. Consequently, with reference to the material to be carried by a tube, the proximal end of the tube is upstream from the distal end of that tube.

To facilitate proper positioning of the distal end of the aerosol delivery tube, the system may include a patient interface. The patient interface may take the form of an infant pacifier. The aerosol delivery tube may pass through the patient interface. The position of the aerosol delivery tube relative to the patient interface may be fixed, for example by a friction fit between that tube and interface.

The invention may be embodied as a method for delivering medication to a patient. Such a method may include:
 (a) generating an aerosol from a medication to provide an aerosolized medication;
 (b) providing a flow of carrier gas;
 (c) using the carrier gas, conveying the aerosolized medication via an aerosol delivery tube that has been positioned inside the patient's airway in order to discharge the aerosolized medication inside the patient's airway.

Generation of the aerosol may occur outside the patient's airway.

A patient interface, which may be shaped like an infant pacifier, may be used to position a distal end of the aerosol delivery tube in the patient's airway. In particular, the distal end of the aerosol delivery tube may be positioned in the oropharyngeal cavity of the patient.

The distal end of the aerosol delivery tube may be positioned at or slightly beyond a distal end of an endotracheal tube. In that arrangement, the aerosol delivery tube may be passed into the endotracheal tube via a port at a proximal end of the endotracheal tube, or through a port of an endotracheal tube adapter, or through a port of a patient respiratory support circuit. The distal end of the aerosol delivery tube may be positioned at or slightly beyond the distal end of the endotracheal tube.

BRIEF DESCRIPTION OF THE DRAWINGS

For a fuller understanding of the nature and objects of the invention, reference should be made to the accompanying drawings and the subsequent description. Briefly, the drawings are:

FIG. 5 is a flow chart depicting a method.

FURTHER DESCRIPTION OF THE INVENTION

A method and system according to embodiments of the present invention foster improved efficiency and safety in administering medications. The invention aerosolizes medication outside the airway of a patient, such as an infant, who may simultaneously require supplemental oxygen and/or application of positive pressure to assist with breathing. The invention is superior to current systems where the medication is aerosolized outside the patient airway because in the invention, the dose of medication is not diluted by the flow of breathing gas and is delivered directly to the airway of the patient. The invention is particularly superior to current systems where the aerosol is generated in the patient airway because the invention allows control of aerosol particle size and offers protection against airway tissue injury from a multi-lumen catheter.

Figure 1:
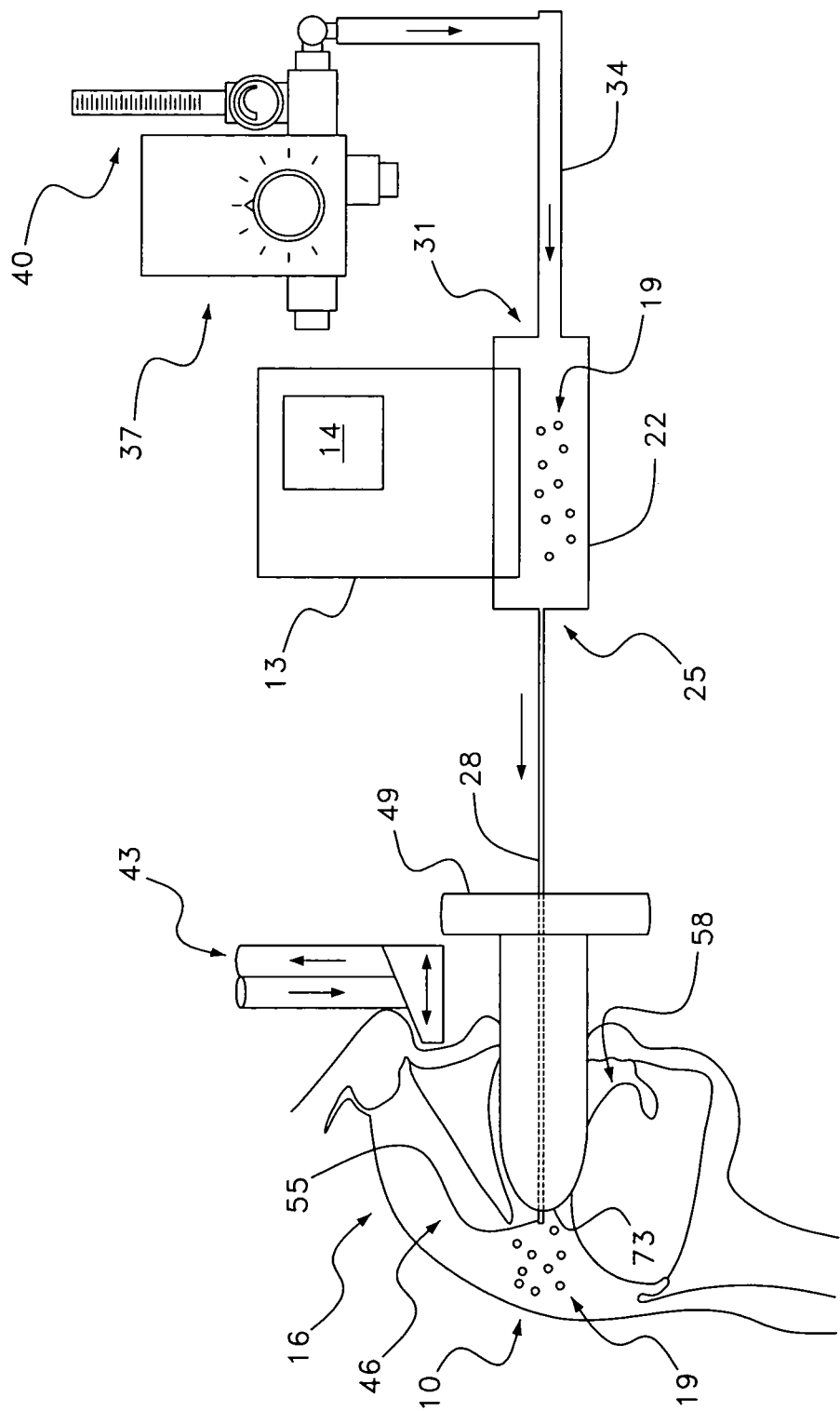
FIG. 1 is a schematic of a system that is in keeping with the invention.

FIG. 1 is a schematic of a system for delivering an aerosol to a patient's oropharyngeal cavity 10. According to an embodiment of the present invention, the medication may be aerosolized by an aerosol generator 13 (e.g. by a vibrating mesh), which is located outside the patient 16. Aerosolized medicament 19 from the generator 13 may be provided to a chamber 22. The chamber 22 may be located proximal to the patient 16, for example within twelve inches, and preferably within six inches, of the patient 16. The chamber 22 has an outlet port 25 that connects to an aerosol delivery tube 28. The chamber 22 has an inlet port 31 that permits a carrier gas supply tube 34 to provide a carrier gas to the chamber 22. The carrier gas supply tube 34 facilitates a flow of the carrier gas from a gas blender 37 to the chamber 22. The flow rate of the carrier gas through the carrier gas supply tube 34 may be set by a flow controller 40. It is believed that for many implementations of the invention, the carrier gas flow rate may be between 0.1 and 2.0 liters per minute. The carrier gas flow provided by the carrier gas supply tube 34 propels the aerosolized medication through the aerosol delivery tube 28 and into the patient 16 at the optimal rate for an individual patient 16. The quantity of medication can be adjusted by turning the generator on or off, as desired. Also, the quantity of medication can be limited by supplying a specified amount of medication to the reservoir 14—when the supply of medication is depleted from the reservoir 14, delivery of the medication to the patient ultimately ceases. The density of the aerosolized medication can be adjusted by setting the flow rate of the carrier gas using the flow controller 40. As such, the aerosol density and the quantity of medication may be independently adjusted to meet individual needs of the patient 16. Also shown in FIG. 1 is a nasal cannula 43, which may be used to deliver bias flow to the nasopharynx 46 for a variety of respiratory support techniques.

For patients 16 who do not require endotracheal intubation, the system according to an embodiment of the present invention conveys aerosolized medications 19 (e.g. aerosolized by a vibrating mesh) into the oropharyngeal cavity 10 through an aerosol delivery tube 28 that passes through a patient interface 49. The patient interface 49 may allow for the patient 16 to exert a holding force via the patient's lips, gums, or teeth. The optimal position of the aerosol delivery tube 28 may be assured by fixing the aerosol delivery tube 28 to the patient interface 49 so that the distal end of the aerosol delivery tube 28 does not significantly move relative to the patient interface 49.

The aerosol delivery tube 28 may be a nasogastric PVC feeding tube, 5 french or larger. Although such an aerosol delivery tube 28 is normally used for feeding, it is believed such a tube could be easily repurposed to serve as the aerosol delivery tube 28 described above. In this manner, the aerosol delivery tube 28 may be selected from readily available, inexpensive items.

Figure 2:
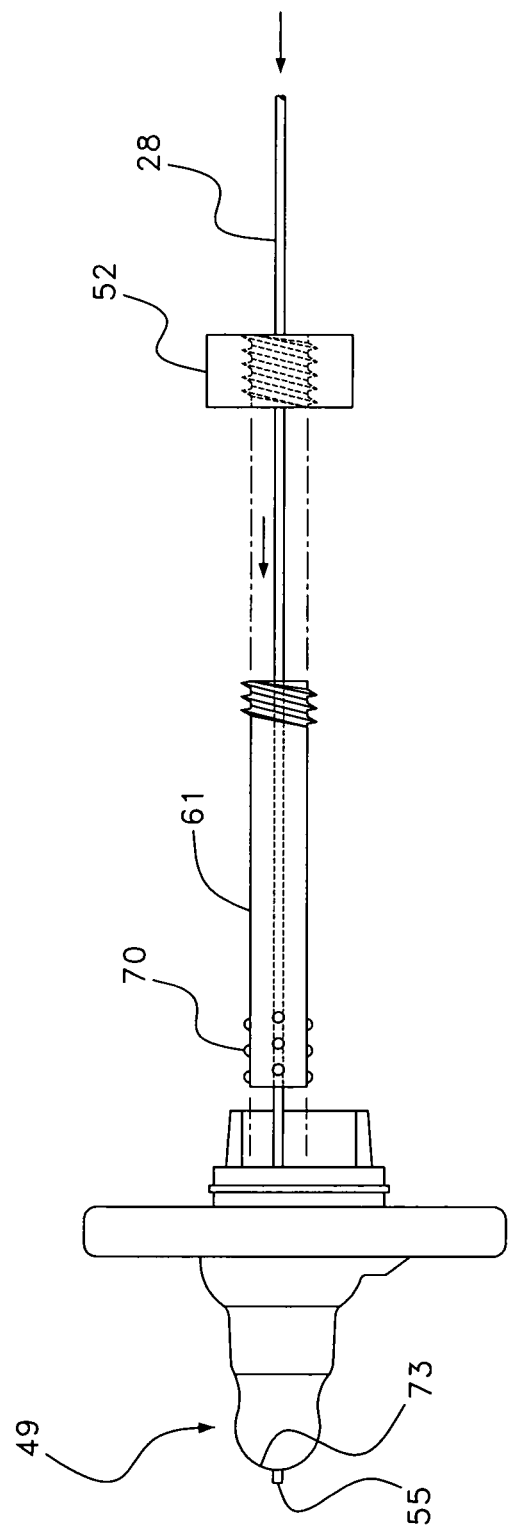
FIG. 2 is an exploded side view depicting a portion of the system depicted in FIG. 1.
Figure 3:
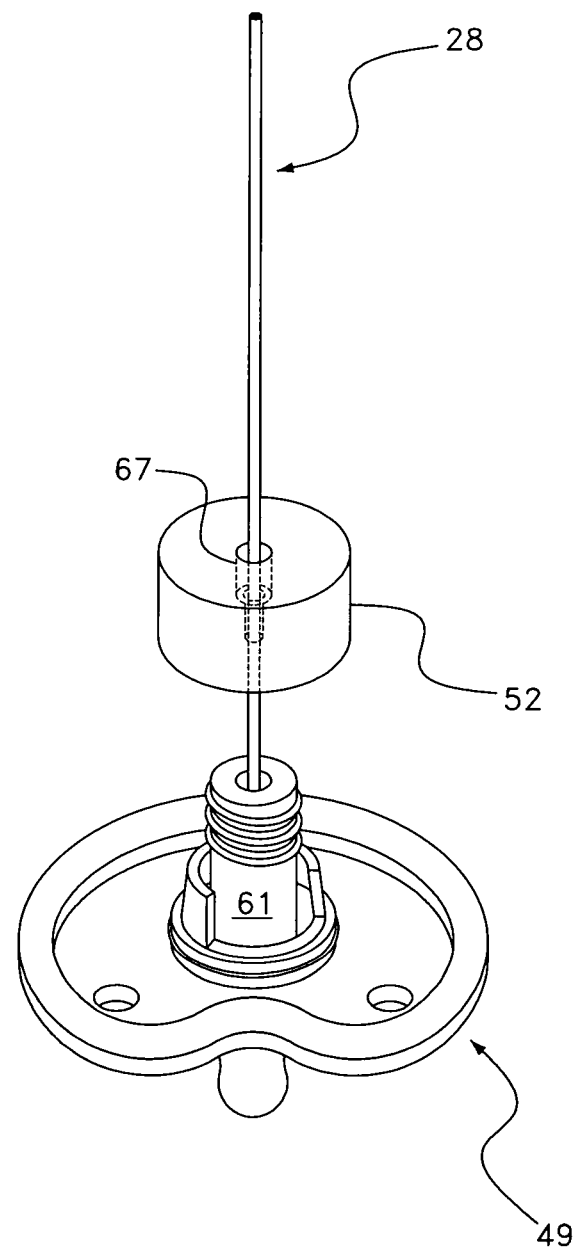
FIG. 3 is an oblique view of the portion depicted in FIG. 2 and which shows some of the components assembled together.

FIGS. 2 and 3 show a patient interface 49, aerosol delivery tube 28 and lock collar 52. By using the patient interface 49, the distal end 55 of the aerosol delivery tube 28 may be placed in the oropharyngeal cavity 10 while assuring that the distal end 55 of the aerosol delivery tube 28 is not obstructed by the tongue 58, buccal mucosa or pharyngeal wall, and also preventing that distal end 55 of the aerosol delivery tube 28 from abrading or piercing the fragile oropharyngeal tissues of the patient 16. Such a method and system is safer than the prior art methods/systems because the aerosol delivery tube 28 used to deliver the aerosolized medication may be prevented from contacting the patient's 16 airway tissue.

The patient interface 49 may be fashioned from a material that allows the patient 16 to comfortably bite down on the patient interface 49. For example, the patient interface 49 may be formed from a semi-flexible material, such as those materials commonly used for a baby pacifier.

FIGS. 2 and 3 show additional details of a portion of the system that is schematically depicted in FIG. 1. In FIGS. 2 and 3, the patient interface 49 is depicted as comprising a plurality of different parts, each of which may be selectively engaged and/or disengaged from the others to provide for easy assembly and/or disassembly. The invention, however, need not be formed from selectively engagable/disengageable parts, and instead may be an integrated set of parts that are not selectively engagable/disengageable.

FIGS. 2 and 3 show a ridged tube 61 that serves to fix the position of the aerosol delivery tube 28 relative to the patient interface 49. A lock collar 52 screws to the ridged tube 61. At least a portion of an interior passage 67 in the lock collar 52 provides a close fit with the aerosol delivery tube 28. Once the lock collar 52 is threaded to the ridged tube 61, the position of the aerosol delivery tube 28 relative to the ridged tube 61 may be held via the close fit in the interior passage 67 of the lock collar 52.

The position of the ridged tube 61 relative to the patient interface 49 may be held by providing a friction-fit between the patient interface 49 and the ridged tube 61. To facilitate that friction-fit, ridges 70 may be provided on an exterior surface of the ridged tube 61 (or ridges may be provided on an interior surface of the patient interface 49). When the ridged tube 61 is inserted into the patient interface 49, the ridges 70 contact an interior surface of the patient interface 49, and the ridged tube 61 may be thereby held relative to the patient interface 49.

When assembled, a distal end 55 of the aerosol delivery tube 28 may extend slightly (e.g. 3 mm or less, with a preferred range of 1 to 3 mm) from the tip 73 of the patient interface 49 so that the medication discharges from the aerosol delivery tube 28 without contacting the patient interface 49. To achieve that arrangement, the ridged tube 61 may be fitted to the patient interface 49. The lock collar 52 may be fitted to the aerosol delivery tube 28. Then, the aerosol delivery tube 28 may be inserted through the ridged tube 61 so that the distal end 55 of the aerosol delivery tube 28 is close to but does not extend from the patient interface 49. As the lock collar 52 is screwed to the ridged tube 61, the aerosol delivery tube 28 is moved relative to the ridged tube 61 and patient interface 49 until the aerosol delivery tube 28 extends slightly from the tip 73 of the patient interface 49.

Figure 4A:
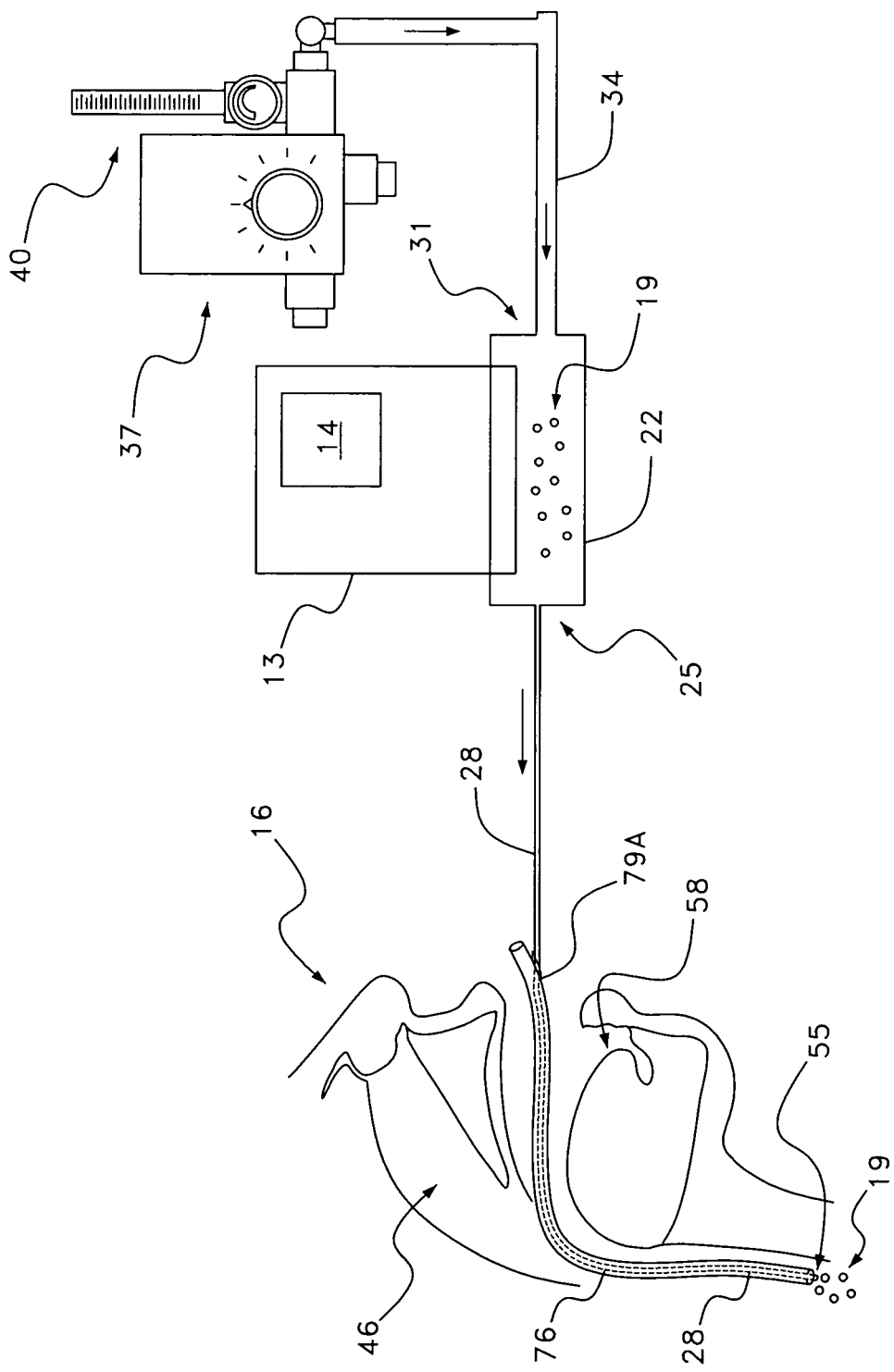
FIGS. 4A, 4B, and 4C are schematics of other systems that are in keeping with the invention.
Figure 4B:
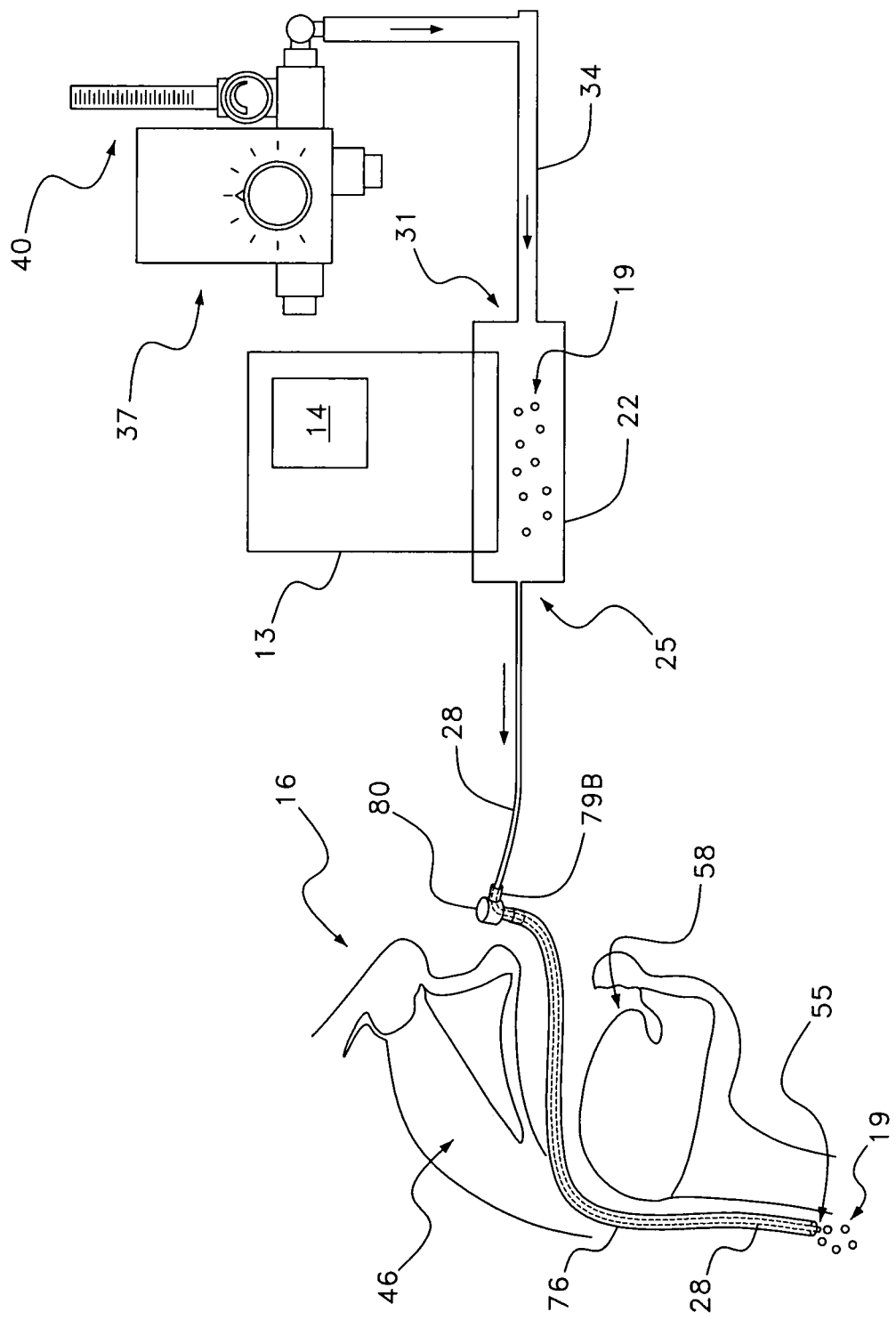
Figure 4C:
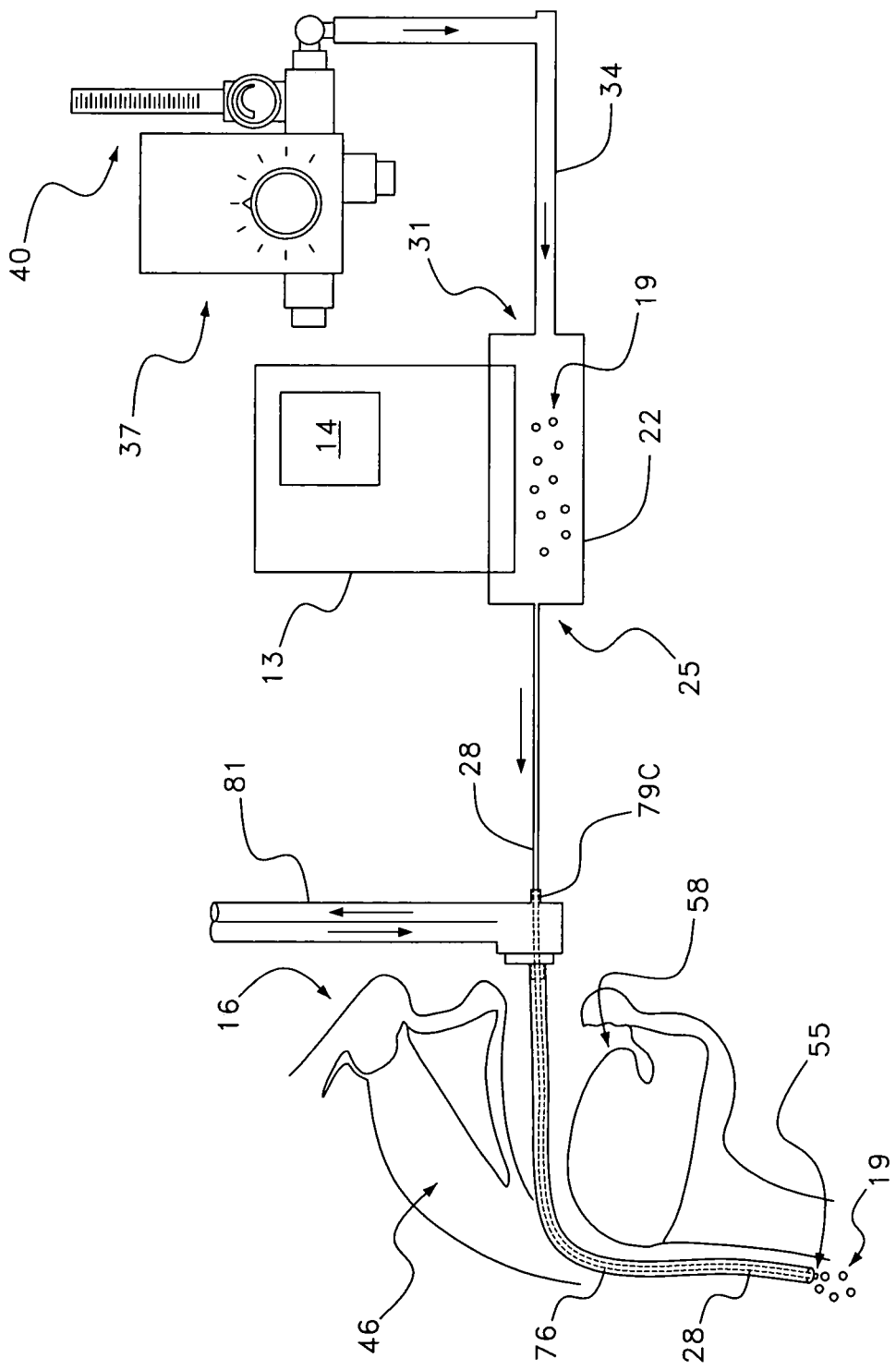

FIGS. 4A, 4B, and 4C are schematics of other systems that are in keeping with the invention for delivering aerosolized medication. In the arrangements depicted in FIGS. 4A, 4B, and 4C, the patient 16 has been intubated. For patients who require endotracheal intubation, an endotracheal tube 76 extends into the patient's 16 airway, and the aerosol delivery tube 28 may be passed through and connected to a port 79A of the endotracheal tube 76 (see FIG. 4A), or passed through and connected to a port 79B of an endotracheal tube adapter 80 (see FIG. 4B), such as a suction or pressure monitoring port of an endotracheal tube adapter 80, or passed through and connected to a port 79C of a patient respiratory support circuit 81 (see FIG. 4C), such as a section or pressure monitoring port of a CPAP (Continuous Positive Airway Pressure) or ventilator circuit. The distal end 55 of the aerosol delivery tube 28 may be sited inside the patient airway at or slightly beyond (e.g. 3 mm or less, with a preferred range of 1 to 3 mm) the distal end of the endotracheal tube 76. Such an arrangement separates respiratory support administration from aerosol medication delivery, which allows care-providers to optimize each separately.

Having described systems that are in keeping with the invention, a method will be described. FIG. 5 depicts steps of a method that is in keeping with the invention. In that method of delivering medication to a patient, an aerosol may be generated 100 from a liquid medication to provide an aerosolized medication. Generating the aerosol occurs outside the patient airway. A carrier gas, such as air or an oxygen/air mixture required by the patient at the time the aerosol is being administered, is provided 103. By flowing 106 the carrier gas, the aerosolized medication may be conveyed 109 via an aerosol delivery tube to a distal end of the aerosol delivery tube, which has been positioned in the patient's airway. The aerosolized medication and carrier gas are discharged 112 inside the patient's airway. To position the distal end of the aerosol delivery tube in the patient's airway, a patient interface, which may be shaped like an infant pacifier, may be used. Alternatively, the aerosol delivery tube may extend through an endotracheal tube so that the distal end of the aerosol delivery tube may be positioned at or slightly beyond a distal end of the endotracheal tube. Such an arrangement within an endotracheal tube may be accomplished by passing the aerosol delivery tube into the endotracheal tube via a port at a proximal end of the endotracheal tube, or through a port of an endotracheal tube adapter, or through a port of a patient respiratory support circuit. The distal end of the aerosol delivery tube may be positioned at the distal end of the endotracheal tube or just slightly beyond (e.g. 3 mm or less, with a preferred range of 1 to 3 mm) the distal end of the endotracheal tube.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A system for delivering medication to a spontaneously breathing, non-intubated patient, comprising:
   an aerosol generator for aerosolizing medication, the aerosol generator being located outside the patient;
   a chamber for receiving aerosolized medication from the aerosol generator;
   a carrier gas supply tube for delivering carrier gas to the chamber;
   an aerosol delivery tube in communication with the chamber for receiving the aerosolized medication and the carrier gas from the chamber, the aerosol delivery tube having a distal end for delivering the aerosolized medication to the patient; and
   a patient interface through which the aerosol delivery tube passes, and the patient interface securing the aerosol delivery tube so that the distal end of the delivery tube is positioned at or slightly beyond a distal end of the patient interface so as to prevent contact with oral tissues of the patient, and when used with a patient the distal end of the aerosol delivery tube is positioned in an oropharyngeal cavity of the patient in order to discharge the aerosolized medication within the patient's oropharyngeal cavity.

2. The system of claim 1, wherein the chamber is located proximal to the patient.

3. The system of claim 1, wherein the patient interface is shaped like an infant pacifier.

4. The system of claim 1, wherein a position of the aerosol delivery tube is fixed relative to the patient interface by a friction fit between the tube and the interface.

5. The system of claim 1, further comprising a breathing gas delivery tube for delivering breathing gas to the patient.

6. The system of claim 1, wherein the aerosol generator includes a vibrating mesh.

7. The system of claim 1, wherein the chamber is located within 12 inches of the patient.

8. The system of claim 1, wherein the chamber is located within 6 inches of the patient.

9. The system of claim 1, further comprising a carrier gas flow rate controller.

10. The system of claim 9, wherein the carrier gas flow rate controller is capable of controlling carrier gas flow to between 0.1 and 2.0 liters per minute.

11. The system of claim 9, wherein a density of the aerosolized medication is adjustable by setting a flow rate of the carrier gas.

12. The system of claim 1, wherein the patient interface is positioned to allow the patient to exert a holding force via the patient's lips, gums, or teeth.

13. The system of claim 1, further comprising a lock collar having a passage through which the delivery tube passes.

14. The system of claim 13, further comprising a ridged tube through which the delivery tube passes, the ridged tube having threads on a first end and ridges on a second end, the ridges engaging the patient interface, and the lock collar is threaded to the threads of the ridged tube.

15. The system of claim 1, further comprising a ridged tube through which the delivery tube passes.

16. The system of claim 15, wherein the ridged tube contacts the patient interface.

17. The system of claim 16, wherein a friction fit exists between the ridged tube and the patient interface.

18. The system of claim 1, wherein the patient interface includes ridges for fixing a position of the patient interface relative to the delivery tube.

19. The system of claim 1, wherein the distal end of the delivery tube extends from the patient interface by 3 mm or less.

20. The system of claim 19, wherein the distal end of the delivery tube extends from the patient interface by a distance of between 1 mm and 3 mm.

21. A method of delivering medication to a spontaneously breathing, non-intubated patient, comprising:
   providing a patient interface through which an aerosol delivery tube passes, which secures a distal end of the delivery tube at or slightly beyond a distal end of the patient interface so as to prevent contact with oral tissues of the patient;
   positioning the patient interface so that the distal end of the aerosol delivery tube is positioned in the patient's oropharyngeal cavity;
   generating an aerosol from a medication to provide an aerosolized medication, wherein generating the aerosol occurs outside the patient;
   providing a flow of carrier gas;
   using the carrier gas, conveying the aerosolized medication via the aerosol delivery tube to the patient's oropharyngeal cavity; and
   discharging the aerosolized medication from the distal end of the aerosol delivery tube to the patient's oropharyngeal cavity.

22. The method of claim 21, wherein the patient interface is shaped like an infant pacifier.

23. The method of claim 21, further comprising fixing a position of the aerosol delivery tube relative to the patient interface by a friction fit between the tube and the interface.

24. The method of claim 21, further comprising providing a breathing gas delivery tube, and delivering breathing gas to the patient via the breathing gas delivery tube.

25. The method of claim 21, wherein the aerosol is generated by a vibrating mesh.

26. The method of claim 21, wherein the flow of carrier gas is between 0.1 and 2.0 liters per minute.

27. The method of claim 21, further comprising adjusting a density of the aerosolized medication by adjusting a flow rate of the carrier gas.

28. The method of claim 21, wherein a patient holds the patient interface by exerting pressure with one or more of the patient's lips, gums, or teeth.

* * * * *